United States Patent [19]

Solomon

[11] 3,944,389

[45] Mar. 16, 1976

[54] DETECTION OF CHLOROMETHYL METHYL ETHER OR BIS-CHLORO-METHYL ETHER

[75] Inventor: Richard A. Solomon, Midland, Mich.

[73] Assignee: The Dow Chemical Company, Midland, Mich.

[22] Filed: July 12, 1973

[21] Appl. No.: 378,480

Related U.S. Application Data

[63] Continuation-in-part of Ser. No. 303,123, Nov. 2, 1973, abandoned.

[52] U.S. Cl. ........... 23/230 R; 23/232 C; 23/230 M
[51] Int. Cl.² ......................................... G01N 31/08
[58] Field of Search .......... 23/232 R, 232 C, 230 R, 23/230 M, 254 E, 254 R, 253 R, 255 R, 255 E

[56] References Cited
UNITED STATES PATENTS 3,807,217   4/1974   Wilkins et al. .................... 23/232 C Primary Examiner—Morris O. Wolk
Assistant Examiner—Barry I. Hollander
Attorney, Agent, or Firm—Earl D. Ayers; Edward E. Schilling; Glenn H. Korfhage

[57] ABSTRACT

Method for quantitatively determining the presence of chloromethyl methyl ether and/or bis-chloromethyl ether in a fluid.

The above compounds are reacted with a reactant from the group consisting of an alkali metal salt of a lower alcohol, an alkali metal salt of phenol or an alkyl phenol, an alkali metal salt of a chlorophenol or bromophenol, an alkali metal salt of an alkoxy phenol, an alkali metal salt of a chlorinated pyridinol, and an alkali metal salt of thiophenol or a chlorinated thiophenol, dissolved in a lower alcohol, to form derivatives which provide suitable stability, specificity and sensitivity when applied to a gas chromatograph utilizing a suitable detector.

22 Claims, 2 Drawing Figures

DETECTION OF CHLOROMETHYL METHYL ETHER OR BIS-CHLORO-METHYL ETHER

This application is a continuation-in-part of application Ser. No. 303,123, filed Nov. 2, 1973, entitled "Analytical Apparatus and Methods", now abandoned.

BACKGROUND OF THE INVENTION

This invention relates to a method for quantitatively determining the amount of chloromethyl methyl ether and bis-chloromethyl ether in a fluid.

Experience indicates that the direct analysis of chloromethyl methyl ether and bis-chloromethyl ether is not adequate in sensitivity, stability or specificity for monitoring small amounts of these compounds in fluids by convenient means such as by using a gas chromatographic column coupled to a suitable detector, for example.

OBJECTS OF THE INVENTION

Accordingly, a principal object of this invention is to provide an improved method of quantitatively determining the amount of chloromethyl methyl ether and/or bis-chloromethyl ether (sometimes hereinafter abbreviated as CMME and bis-CME, respectively) in a fluid.

Another object of this invention is to provide an improved method for monitoring the presence of chloromethyl ether and/or bis-chloromethyl ether in air down to the level of parts per billion, or less.

STATEMENT OF INVENTION

In accordance with this invention, chloromethyl methyl ether and/or bis-chloromethyl ether, occurring in either liquid or gaseous medium, are reacted with a material from the group consisting of an alkali metal salt of a lower alcohol, an alkali metal salt of phenol or an alkyl phenol, an alkali metal salt of a chlorophenol or bromophenol, an alkali metal salt of an alkoxy phenol, an alkali metal salt of a chlorinated pyridinol, and an alkali metal salt of thiophenol or a chlorinated thiophenol, dissolved in a lower alcohol to form a stable derivative (with enhanced sensitivity) for analytical use. The derivative(s) is then passed through a gas chromatograph having a suitable detector. The detector output signal is then coupled, usually through an amplifier, to a recorder or other readout device.

BRIEF DESCRIPTION OF THE DRAWING

The invention, as well as additional objects and advantages thereof, will best be understood when the following detailed description is read in connection with the accompanying drawing in which.

DETAILED DESCRIPTION OF THE DRAWING

Figure 1:
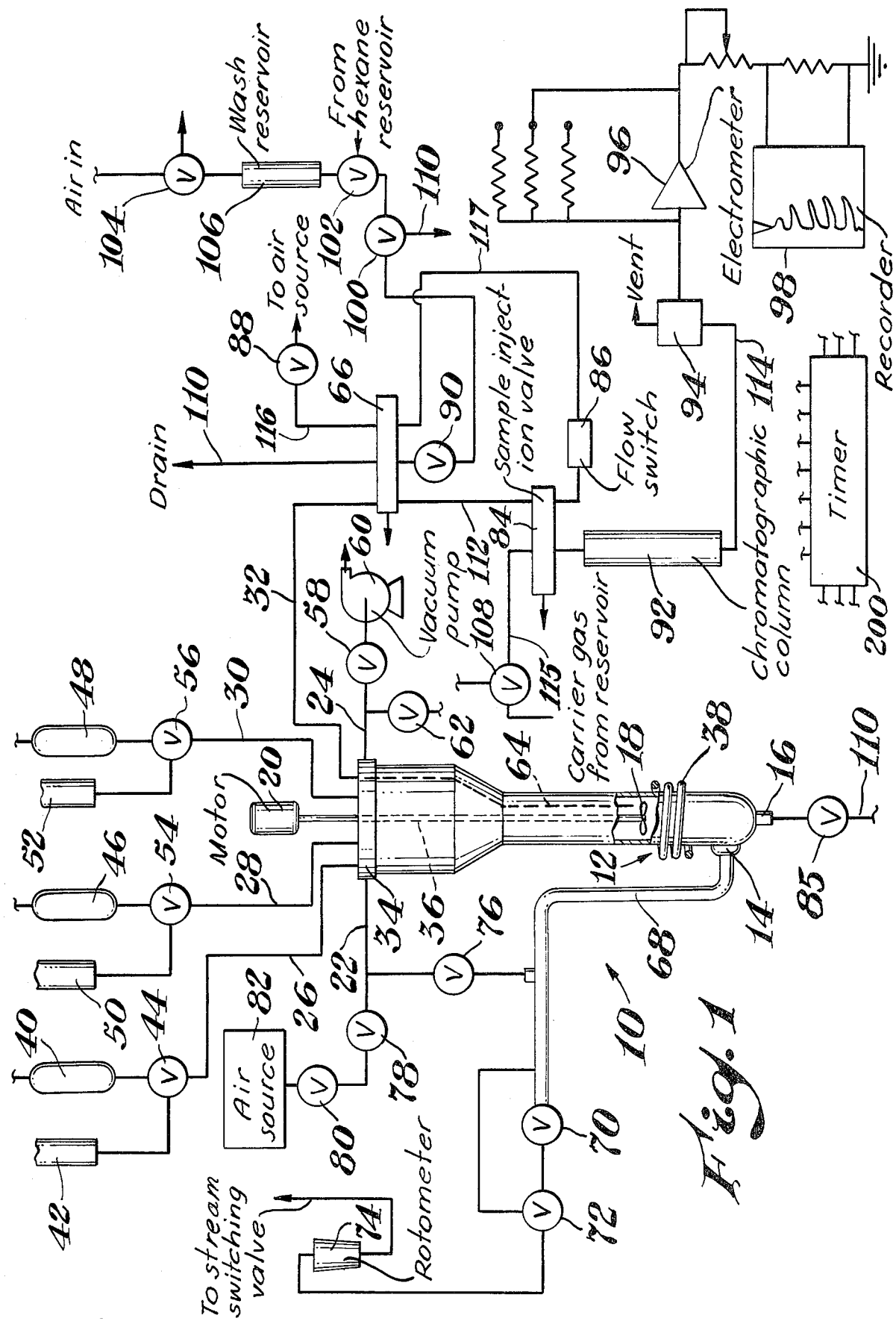
FIG. 1 shows, in diagrammatical form, apparatus for use in analyzing gas samples in accordance with this invention.

Referring to FIG. 1 of the drawing, there is shown apparatus for analyzing gas samples, indicated by the numeral 10, including a scrubber 12 having an inlet 14 and an outlet 16 near and at the bottom thereof, respectively. The scrubber 12 has a stirrer 18 therein which is actuated by an externally located motor 20. Six lines 22, 24, 26, 28, 30, 32 extend through the closed top 34 of the scrubber, as does the shaft 36.

A heat tape 38 surrounds part of the lower part of the scrubber 12.

The line 26 is coupled to a measuring pipet 40 and a constant level tank 42 through a three way valve 44. The lines 28 and 30 are similarly coupled to pipets 46 and 48, respectively, and to tanks 50 and 52, respectively, through the three way valves 54 and 56, respectively.

The line 24 is coupled through a valve 58 to a vacuum pump 60. The line 24 may also be opened to the atmosphere through the valve 62.

The line 32 is coupled to the dip pipe 64 and to a six port chromatograph valve 66.

A line 68 is coupled to the scrubber inlet 14 and, through valve 70, flow control valve 72, and rotometer 74, to an air source (via a stream switching valve, for example). The line 68 is also coupled to the line 22 through valve 76. The line 22 is also coupled through needle valve 78 and valve 80 to a source 82 of pressurized air.

The outlet 16 of the scrubber 12 opens through the valve 85 to drain 110.

Carrier gas from a reservoir (not shown) is coupled through valve 108 and line 115 to the sample injection valve 84 and thence through the chromatographic column 92. The line 112 connects the line 32 through the chromatograph valve 66 to the sample injection valve 84.

The output of the chromatographic column 92 is coupled through the line 114 to an electron capture or other suitable detector 94 whose output is coupled to an electrometer 96 or other suitable amplifier and thence to a recorder 98 or other readout device.

A suitable solvent such as hexane, for example, from a reservoir (not shown) is applied to a wash reservoir 106 through three way valve 102. The upper end of the reservoir 106 is coupled to a three way valve 104 which is also coupled to an air source (like the source 82).

The other side of the valve 102 is coupled through valve 100 and valve 90 to the multiport chromatographic valve 66. Valve 100 may also be coupled to a drain 110.

The sample injection valve 84 is coupled through the line 117 and flow switch 86 to the chromatographic valve 66.

A line 116 is coupled through valve 88 between an air source (not shown) and the multiport chromatographic valve 66.

OPERATION OF FIG. 1 APPARATUS

At the start of the analytical cycle the scrubber 12 is empty. Valve 54 is actuated to drain a reagent (which will react with CMME or bis-CME to form a derivative) from pipet 46 into the scrubber and is then closed. Pipet 46 has been filled from the constant level tank 50. At this time valve 58 is opened to allow vacuum to be pulled on the scrubber 12. Sample air is then pulled through rotometer 74 and flow controller 72 through the reagent in the bottom of the scrubber to the top of the scrubber and out the tubing line 24. After a preset length of time (usually about 8 minutes), valve 62 is opened to partially or fully relieve the vacuum which will reduce air flow through scrubber 12. Heat is applied to the reagent in the scrubber by external heat tape 38 wrapped around the bottom of scrubber 12.

Sample volume is dependent upon concentration of CMME and bis-CME in the air sample. For 10 ppb or less a sample size of 10 to 40 liters can be used. For higher concentrations a correspondingly smaller sample should be taken.

Stirrer motor 20 is activated simultaneously with heating to provide agitation. After the liquid in the scrubber 12 is brought to slightly above room temperature (on time basis by experience), valve 44 is actuated to drain water into the scrubber 12 from measuring pipet 40 which is filled from constant level tank 42.

After water has been admitted, valve 56 is actuated to drain into the scrubber a solvent such as hexane from measuring pipet 48 which has been filled from constant level tank 52. At this time, valve 58 is closed to remove all vacuum from the scrubber. Stirrer motor 20 continues to run to mix the scrubber solution adequately. Valve 80, which is connected to a pure filtered pressurized air source from an air tank, for example, is opened. Valve 78 is a needle valve that restricts air flow to low flow rates. After solutions are mixed adequately in the scrubber 12, stirrer motor 20 is stopped and the hexane and water (or other lower alcohol) methanol mixture allowed to separate, with the hexane then floating on top.

After sufficient time (about 2 minutes) has elapsed for the solution to separate, valve 62 is closed as are valves 44, 54, and 56 if the latter three valves have not already been actuated to refill pipets 40, 46, 48. The stream switching valve (or equivalently, valves 70 and 72) is closed and valve 76 is opened to maintain equilibrium between the pressure in line 68 and that in the scrubber 12. The increasing air pressure within the scrubber 12 then forces substantially all the hexane up dip pipe 64 which is adapted to terminate in the hexane layer just above the liquid-liquid interface. Since the pressure is equalized in line 68 and the scrubber 12, the level of the liquid-liquid interface is maintained constant just below the end of the dip pipe 64, while the major portion of the hexane is driven up the dip pipe.

From the dip pipe 64, the hexane is pushed by pressure through the transfer line 32 through a six port chromatograph valve 66 and through sample injection valve 84 to flow switch 86.

As soon as liquid reaches flow switch 86, chromatograph valve 66 and valves 88 and 90 are actuated. Valve 88 is connected to a pressurized, filtered source of air. Valve 90 is normally open to drain to allow air to escape while hexane is transferred. Actuation of valves 66, 90 and 88 places a liquid filled line on both sides of sample valve 84 under pressure to prevent air bubbles forming in the liquid. After air pressure is applied to the liquid, valve 84 is actuated to inject a liquid sample into chromatograph column 92 where a typical gas chromatograph separation is completed (Beckman Model 320 DF or Bendix Model 6000 may be used, for example). Components from the column 92 are eluted into a suitable detector 94 such as an electron capture detector, for example, which when a halogenated compound is present will cause a decrease of electrical current through the detector. The small decrease in current is sensed by an electrometer 96, amplified and displayed on recorder 98.

A short time after a sample is injected, valve 90 is opened and hexane that was trapped in the transfer tubing before and after the sample injection valve, is forced by air pressure into drain 110 through valve 100. After a short period of time, valve 88 is shut off and valve 66 is actuated to its original position. Valve 90 is left open ready for the next transfer of liquid.

At this time, valve 85 is opened to the drain 110 to remove residual liquid from the scrubber 12. At this same time, valves 100 and 102 are actuated. After a small time delay, valve 104 is also actuated. Valve 104 is connected to a source of clean pressurized air and to the top of wash reservoir 106. Wash reservoir 106 has been filled previously through valve 102 with hexane from reservoir 52. Pressurized air then forces the hexane from wash reservoir 106 through valves 102, 100, 90, valve 66, flow switch 86, valve 84, again through valve 66, through transfer line 32 to the scrubber 12 and out valve 85 to drain 110. This wash effectively removes any residual sample left in any valves or in the scrubber 12.

After hexane has been completely drained through the system, valve 104 closes followed by closure of valves 100, 102 and 85. Wash reservoir 106 fills again from the reservoir 52 through valve 102 to be ready for another wash cycle.

Pressure regulator 108 is part of the gas chromatograph unit and is used to control the flow of carrier gas.

The system is then ready for preparation of another sample.

The various valves are remotely actuated valves. They and the motor 20 are actuated by means of a sequential timing device 200 of any of a number of types well-known to those skilled in the instrumentation art.

One reagent used in reservoir 50 is prepared by dissolving 2.4 g of sodium methoxide and 0.5 g of chlorinated phenol per 100 ml of methanol solvent. Since some of the sodium methoxide reacts with the phenol to form the phenate, the resulting reagent contains both sodium chlorophenate and sodium methoxide dissolved in methanol. Formed as derivatives of CMME and bis-CME, respectively, when such a reagent is employed are chlorophenoxymethyl methyl ether and the mixed derivative chlorophenoxymethyl methoxymethyl ether, which are both readily detectable with, for example, an electron capture detector.

The analysis of this invention is based upon the reaction of chloromethyl methyl ether (CMME) and/or bis-chloromethyl ether (bis-CME) to form a derivative which is suitable for analyses by gas chromatographic means. To assure quantitative formation of the respective derivative, an amount of derivatizing agent in excess of the amount theoretically required for stoichiometric reaction is employed, with at least a ten-fold excess being preferred. Reactions for the formation of these derivatives are shown in the chart below:

| Reactant | Type of Sample | Derivative From Reacting With | | Detector |
|---|---|---|---|---|
| | | Chloromethyl Methyl Ether | bis-Chloromethyl Ether | |
| RONa | Liq. or Gas | $ROCH_2OCH_3$ $R = C_1 - C_5$ | $ROCH_2OCH_2OR$ | FID |

| Reactant | Type of Sample | Derivative From Reacting With Chloromethyl Methyl Ether | Derivative From Reacting With bis-Chloromethyl Ether | Detector |
|---|---|---|---|---|
| Phenyl-ONa | Liq. or Gas | Phenyl-O-CH$_2$OCH$_3$ | Phenyl-OCH$_2$OCH$_2$O-Phenyl | FID |
| R-substituted Phenyl-ONa | Liq. or Gas | R-substituted Phenyl-O-CH$_2$OCH$_3$ | R-substituted Phenyl-OCH$_2$OCH$_2$O-Phenyl-R | FID |
| | | R = C$_1$ – C$_4$ could be substituted at more than one ring position | | |
| X-substituted Phenyl-ONa | Gas | X-substituted Phenyl-O-CH$_2$OCH$_3$ | X-substituted Phenyl-OCH$_2$OCH$_2$O-Phenyl-X | EC |
| | | x = Cl or Br (1 – 5 atoms on ring) | | |
| Cl, OCH$_3$-substituted Phenyl-ONa | Liq. or Gas | Cl, OCH$_3$-substituted Phenyl-OCH$_2$OCH$_3$ | Cl, OCH$_3$-substituted Phenyl-OCH$_2$OCH$_2$O-Phenyl-Cl, OCH$_3$ | |
| | | Cl: 1 – 3 atoms substituted on ring | | |
| X-substituted Pyridyl-ONa | Gas | X-substituted Pyridyl-OCH$_2$OCH$_3$ | X-substituted Pyridyl-OCH$_2$OCH$_2$O-Pyridyl-X | EC |
| | | x = 1 – 4 Cl atoms substituted on ring | | |
| Phenyl-SNa | Liq. or Gas | Phenyl-SCH$_2$OCH$_3$ | Phenyl-SCH$_2$OCH$_2$S-Phenyl | FP or FID |
| X-substituted Phenyl-SNa | Liq. or Gas | X-substituted Phenyl-SCH$_2$OCH$_3$ | X-substituted Phenyl-SCH$_2$OCH$_2$S-Phenyl-X | FP or EC |
| | | x = 1 thru 4 Cl atoms | | |

In the above chart
FID means hydrogen flame ionization detector;
EC means electron capture detector; and
FP means flame photometric detector.

On the chart, if "liq." or "gas" is underlined, that indicates the preferred form of the sample used in the analysis.

In the reactions designated in the above chart, in each case the reagent is dissolved in a lower alcohol, preferably the corresponding alcohol.

The derivatizing reagent may also be prepared by dissolving an alkali metal in the desired alcohol. For example, sodium metal dissolved in methanol or an other lower alcohol. Potassium, lithium or cesium metal may also be used.

Chromatographic conditions used for the trace analysis work require glass columns packed with 0.1% OV-17+0.1% QF-1 on 120/140 GLC-110. Preferably the liquid phase materials, OV-17 and QF-1, are distributed rather thinly over the glass beads, GLC-110 or other solid phase such as Chromosorb silicate to provide what is known in the trade as a lightly loaded column. On-column injection technique whereby the sample is vaporized at column temperatures should be used to prevent degradation of the derivatives of CMME and bis-CME. The column temperature is 140° C., and the flow rate approximately 40 ml/min. of carrier gas. These conditions should be used as a general rule when chromatographing derivative compounds of the size of trichlorophenate and larger. For the lower molecular weight derivatives, standard metal columns and packings have proven sufficient.

The derivatives impart high sensitivity, stability and specificity to the CMME and bis-CME when using a suitable detector (the electron capture detector is a common gas chromatograph detector which is very specific for chlorine containing compounds, for example). However, the electron capture detector is not very responsive to CMME and bis-CME when chromatographed directly.

The hydrogen flame ionization detector is commonly used where the CMME or bis-CME level is from the parts per million to percent range. The electron capture detector is particularly useful where the concentration is from less than one part per billion to the low parts per million range. The flame photometric detector, which is logarithmically linear for the detection of sulfur compounds, is useful where the concentration is from the parts per billion to the parts per million range.

Thus, the type of reagent used and the detector chosen depend on the nature of the sample (present in liquid or gas form) and the suspected concentration of CMME or bis-CME in the sample.

The apparatus shown in FIG. 1 is adapted for use especially for analysis of air samples.

Figure 2:
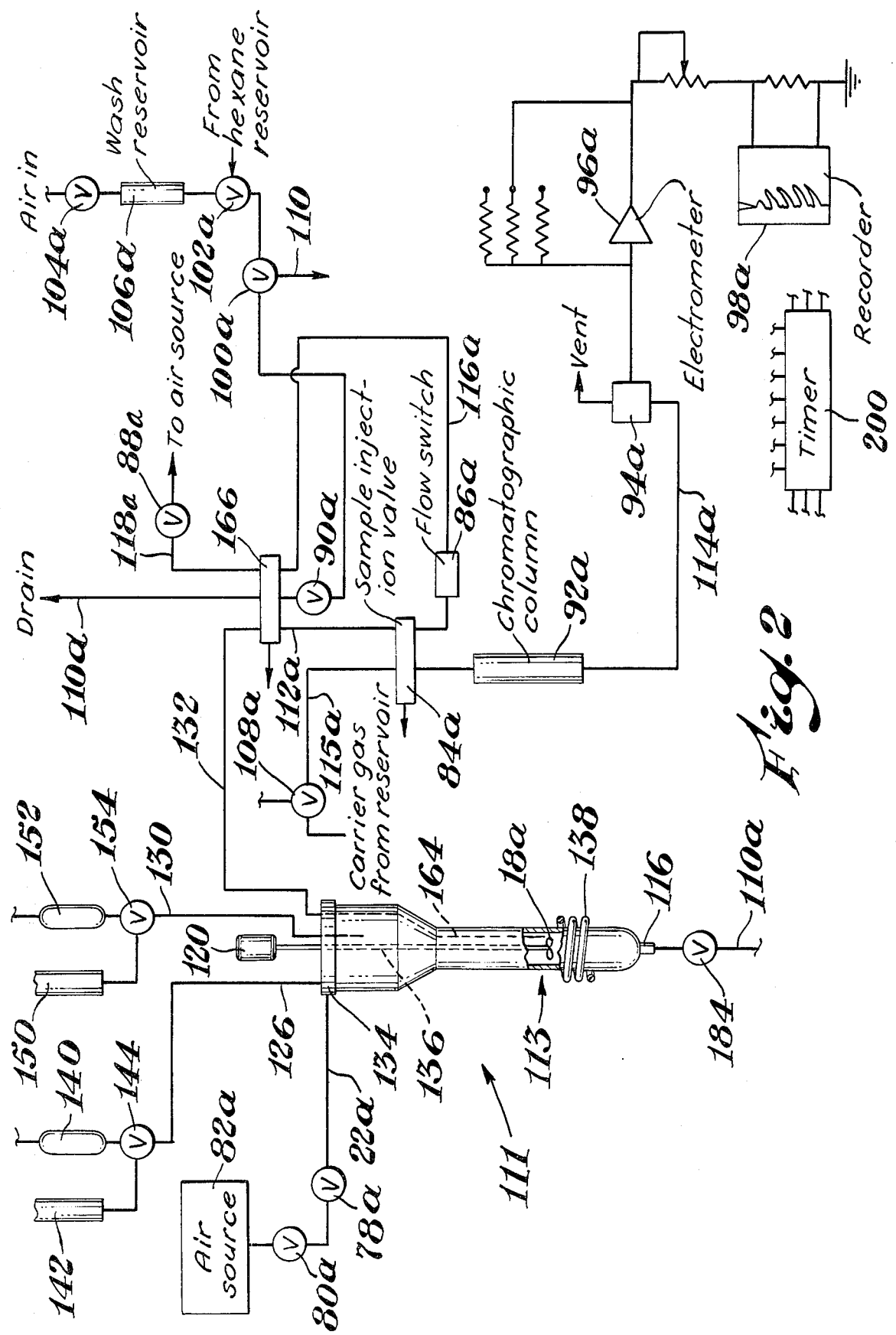
FIG. 2 shows, in diagrammatical form, apparatus for analyzing liquid samples in accordance with this invention.

For use with liquid samples, the somewhat simplified apparatus of FIG. 2 may be used.

Referring to FIG. 2, there is shown apparatus, indicated generally by the numeral 111, including a reaction vessel 113 having an outlet 116 at the bottom thereof. The reaction vessel 113 has a stirrer 18a which is actuated by the externally located motor 120. Lines 126, 130 and 132 extend through the closed top 134 of the reaction vessel 113, as does the shaft 136.

A source of pressurized air 82a is coupled through the needle valve 80a, shutoff valve 78a and line 22a to the interior of the reaction vessel 113.

A heat tape 138 surrounds part of the lower part of the reaction vessel 113.

The line 126 is coupled to a measuring pipet 140 and the constant level tank 142 through a three way valve 144. The line 130 is similarly coupled to a measuring pipet 152 and constant level tank 150 through the three way valve 154.

The line 132 is coupled to a dip pipe 164 in the reaction vessel 113 and to a six port chromatograph valve 166.

The outlet 116 of the reaction vessel 113 opens through the valve 184 to drain 110a.

Carrier gas from a reservoir (not shown) is coupled through valve 108a and line 115a to the sample injection valve 84a and thence through the chromatographic column 92a. The line 112a connects the line 132 through the chromatographic valve 166 to the sample injection valve 84a.

The output of the chromatographic column 92a is coupled through the line 114a to a suitable detector 94a whose output is coupled to an electrometer 96a or other suitable amplifier and thence to a recorder 98a or other readout device.

A suitable solvent, such as hexane, for example, from a reservoir (not shown) is applied to a wash reservoir 106a through the three way valve 102a. The upper end of the reservoir 106a is coupled to a three way valve 104a which is also coupled to an air source (not shown).

The other side of the valve 102a is coupled through valve 100a and valve 90a to the multi-port chromatographic valve 166. Valve 100a may also be coupled to a drain 110.

The sample injection valve 84a is coupled through the line 116a and flow switch 86a to the chromatographic valve 166.

A line 118a is coupled, through valve 88a, between an air source (not shown) and the multi-port chromatographic valve 166.

At the start of the analytical cycle the reaction vessel 113 is empty. Valve 144 is actuated to drain reagent from the pipet 140 into the vessel 113 and is then closed. Pipet 140 has been filled from the constant level tank 142. The valve 154 is then opened to drain sample liquid from the pipet 152 through the line 130 into the reaction vessel 113. The valve 154 is then closed. The contents of the vessel 113 are then heated (via tape 138) and stirred by the stirrer 18a. After being stirred for a suitable time to form the derivative, the liquid is driven upwardly through the dip pipe 164 and line 132 to the multi-port chromatographic valve 166 by opening the shutoff valve 78a to pressurize the interior of the vessel 113.

From this point, the operation of the embodiment shown in FIG. 2 is the same as for the apparatus of FIG. 1.

As alternatives to the use of hexane as a solvent, one may use benzene, decane, octane, iso-octane, pentane, alkyl benzenes, or mixtures thereof, for example. Similar solvents with suitable viscosity may also be used.

As an example of the analysis of a liquid sample, the analysis is performed by adding the liquid sample in a ratio of 0.1 gm to 10 ml of derivatizing solution (sodium ethoxide, about 3.5 grams-dissolved in 100 ml. of ethanol). The sample is stirred and heated. The solution is then injected into the chromatograph. The components are then separated on the column and eluted into a suitable detector (FID, for example) for quantitation.

The method of this invention is also useful in process applications where it is desirable to determine the amount of bis-chloromethyl ether and/or chloromethyl methyl ether, along with other formaldehyde generating components, present in a chloromethyl methyl ether liquid stream in order to accurately balance chloromethylating reactions in the production of electroconductive and ion exchange resins.

For example, a liquid mixture of methylal, methanol, chloromethyl methyl ether and ethylene dichloride are separated and determined using a 15 ft. × ⅛ inch stainless steel column packed with 25% LAC-2R446 + 2% $H_3PO_4$ on 100/120 Chromosorb WHP. The column temperature is 70° C., and the flow rate approximately 30 ml./min of carrier gas. Bis-chloromethyl ether is determined by increasing the column temperature to 120° C.

I claim:
1. A method to determine the presence of chloromethyl methyl ether or bis-chloromethyl ether in a fluid, comprising reacting chloromethyl methyl ether or bis-chloromethyl ether from said fluid with an amount in excess of the stoichiometric amount of an alkali metal salt of an organic hydroxy compound of the formula
   1. R—OH wherein R is lower alkyl, phenyl, chlorophenyl, bromophenyl, alkoxy phenyl, or alkyl phenyl or
   2. thiophenyl or chlorinated thiophenyl or
   3. chlorinated pyridinyl, said compound being dissolved in lower alcohol, running the reaction product through a suitable gas chromatographic column, then passing the eluted components therefrom through a detector and displaying the output of said detector on a suitable readout device.

2. The method of claim 1, wherein said reagent is an alkali metal salt of a lower alcohol.

3. The method of claim 1, wherein said reagent is an alkali metal salt of phenol or an alkyl phenol.

4. The method of claim 1, wherein said reagent is an alkali metal salt of a chlorophenol.

5. The method of claim 1, wherein said reagent is an alkali metal salt of a bromophenol.

6. The method of claim 1, wherein said reagent is an alkali metal salt of an alkoxy phenol.

7. The method of claim 1, wherein said reagent is an alkali metal salt of thiophenol or of a chlorinated thiophenol.

8. The method of claim 1, wherein said reagent is an alkali metal salt of a chlorinated pyridinol.

9. The method of claim 1, wherein said fluid is air.

10. The method of claim 1, wherein said fluid comprises a liquid mixture of ethylene dichloride, methanol, methylal and chloromethyl methyl ether.

11. The method of claim 1, wherein said compound is present in at least 10 times the stoichiometric amount needed for the reaction with chloromethyl methyl ether or bis-chloromethyl ether.

12. The method of claim 1, wherein said compound is sodium phenate.

13. The method of claim 1, wherein said compound is sodium methoxide.

14. The method of claim 1, wherein said compound is sodium ethoxide.

15. The method of claim 1, wherein said compound is the sodium salt of 2,4,6-trichlorophenol.

16. The method of claim 1, wherein said compound is a sodium salt of a chlorinated phenol.

17. A method to determine the presence of chloromethyl methyl ether or bis-chloromethyl ether in a gas comprising passing a predetermined amount of gas through a confined stoichiometric excess of an alkali metal salt of an organic hydroxy compound selected from the group consisting of a lower alcohol, phenol, a chlorophenol, a bromophenol, an alkyl phenol, an alkoxy phenol, a chlorinated pyridinol, thiophenol or a chlorinated thiophenol which hydroxy compound is dissolved in lower alcohol, adding water and hydrocarbon solvent to said compound, agitating the mixture of compound, water and solvent, partitioning said hydrocarbon solvent from the remainder of said mixture, withdrawing part of said hydrocarbon solvent and applying said withdrawn part to suitable gas chromatographic apparatus, applying eluted components from said chromatographic apparatus to a suitable detector providing an output signal, and applying said output signal to a suitable readout device.

18. The method of claim 17, wherein said detector is an electron capture detector.

19. The method of claim 17, wherein said hydrocarbon solvent is hexane.

20. The method of claim 17, wherein said gas chromatographic apparatus includes a lightly loaded glass chromatographic column.

21. The method of claim 17, wherein said compound is heated before said water and solvent are added.

22. A method of determining the presence of chloromethyl methyl ether or bis-chloromethyl ether in a liquid, comprising mixing a predetermined amount of said liquid with a stoichiometric excess amount of an alkali metal salt of a lower alcohol, said salt being dissolved in a lower alcohol, to form a derivative compound, running said derivative through a suitable gas chromatographic apparatus, passing material eluting from said apparatus through a suitable detector providing an output signal, and recording said output signal on a suitable readout device.

* * * * *

UNITED STATES PATENT AND TRADEMARK OFFICE
CERTIFICATE OF CORRECTION

PATENT NO. : 3,944,389
DATED : March 16, 1976
INVENTOR(S) : Richard A. Solomon

It is certified that error appears in the above-identified patent and that said Letters Patent are hereby corrected as shown below:

In the title, "Bis-Chloro-Methyl" should read --Bis-Chloromethyl--.

Column 2, line 61, insert --the-- after "through", first occurrence.

Column 3, line 23, insert a slash --/-- after "water"; also delete "(or other lower alcohol)" after "water" and insert --(or other lower alcohol)-- after "methanol".

In the chart, underline the word "Liq." in the first three reactions and underline the word "Gas" in reactions 5, 7 and 8.

Column 9, Claim 17, line 3, insert the word --said-- after "of".

Signed and Sealed this

Twenty-fourth Day of August 1976

[SEAL]

Attest:

RUTH C. MASON
*Attesting Officer*

C. MARSHALL DANN
*Commissioner of Patents and Trademarks*